United States Patent

[11] Patent Number: 5,837,796
[45] Date of Patent: Nov. 17, 1998

Scholl et al.

[54] POLYISOCYANATES CONTAINING ISOCYANURATE GROUPS AND PREPARED BY TRIMERIZING ALKYL-SUBSTITUTED CYCLOALIPHATIC DIISOCYANATES

[75] Inventors: Hans-Joachim Scholl; Bernhard Jansen, both of Köln; Rolf-Volker Meyer, Leverkusen, all of Germany

[73] Assignee: Bayer Aktiengesellschaft, Leverkusen, Germany

[21] Appl. No.: 883,477

[22] Filed: Jun. 25, 1997

[30] Foreign Application Priority Data

Jul. 10, 1996 [DE] Germany ............. 196 27 825.2

[51] Int. Cl.$^6$ ................... C08G 18/79
[52] U.S. Cl. ............ 528/73; 528/44; 252/182.2; 252/182.21; 544/221; 544/222
[58] Field of Search .......... 528/44, 73; 252/182.2, 252/182.21; 544/221, 222

[56] References Cited

U.S. PATENT DOCUMENTS 4,552,946 11/1985 Scholl et al. ................ 528/67

FOREIGN PATENT DOCUMENTS

| 1207340 | 7/1986 | Canada . |
| 1239415 | 7/1988 | Canada ................ 260/456.4 |
| 1248552 | 1/1989 | Canada ................ 260/605.8 |
| 3317875 | 11/1984 | Germany . |

OTHER PUBLICATIONS

Hackh's Chemical Dictionary, McGraw Hill Book Company, Fourth Edition, p. 326; 1969.
H.J. Laas, R.Halpaap & J. Pedain, J. Prakt. Chem. 336 (month unavailable) 1994, 185–200.

*Primary Examiner*—Rachel Gorr
*Attorney, Agent, or Firm*—Joseph C. Gil; Thomas W. Roy

[57] ABSTRACT

The present invention relates to a process for preparing polyisocyanates containing isocyanurate groups by trimerizing a portion of the isocyanate groups of an organic polyisocyanate component containing a) one or more diisocyanates corresponding to formula (1)

$$OCN-\text{C}_6H_9(R)-NCO \quad (1)$$

wherein

R represents a saturated, straight-chain, aliphatic hydrocarbon group having 8 to 15 carbon atoms and optionally b) up to 95 NCO equivalent-%, based on the total equivalents a) and b), of one or more organic polyisocyanates other than a), in the presence of trimerization catalysts and terminating the trimerization reaction at any desired degree of trimerization.

The invention also relates to the polyisocyanates containing isocyanurate groups obtained by this process and to their use, optionally in excess starting polyisocyanates and optionally blocked with blocking agents for isocyanate groups, as an isocyanate component for preparing polyisocyanate addition products.

11 Claims, No Drawings

: 
POLYISOCYANATES CONTAINING ISOCYANURATE GROUPS AND PREPARED BY TRIMERIZING ALKYL-SUBSTITUTED CYCLOALIPHATIC DIISOCYANATES

BACKGROUND OF THE INVENTION

1. Field of the Invention

The present invention relates to a process for preparing polyisocyanates containing isocyanurate groups by partially trimerizing the isocyanate groups of alkyl-substituted cycloaliphatic diisocyanates, to the resulting polyisocyanates and to their use for preparing polyisocyanate addition products.

2. Description of the Prior Art

Many processes for preparing polyisocyanates containing isocyanurate groups have been disclosed (J. H. Saunders and K. C. Frisch, Polyurethanes Chemistry and Technology, part I, p. 94 et seq., 1962). Another summary of processes for preparing cycloaliphatic and mixed cycloaliphatic/aliphatic polyisocyanates containing isocyanurate groups has been published more recently (H. J. Laas, R. Halpaap and J. Pedain, J. prakt. Chem. 336 (1994), 185–200). Many different types of trimerization catalysts have been described for these processes in the references mentioned.

There are still a number of disadvantages associated with many polyisocyanates containing isocyanurate groups which require improvement. For example, they have compatibility problems when mixed with other components and the pot life of these mixtures are too short, especially when used as bonding agents.

An object of the present invention is to provide new polyiso-cyanates containing isocyanurate groups which can be obtained in an uncomplicated manner, have improved compatibility and have improved useful potlives. This object can be achieved with the process according to the invention, which is described in more detail below.

SUMMARY OF THE INVENTION

The present invention relates to a process for preparing polyisocyanates containing isocyanurate groups by trimerizing a portion of the isocyanate groups of an organic polyisocyanate component containing a) one or more diisocyanates corresponding to formula (1)

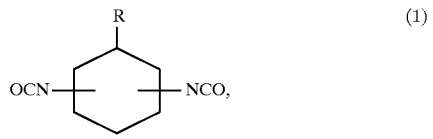

wherein

R represents a saturated, straight-chain, aliphatic hydrocarbon group having 8 to 15 carbon atoms and optionally b) up to 95 NCO equivalent-%, based on the total equivalents a) and b), of one or more organic polyisocyanates other than a), in the presence of trimerization catalysts and terminating the trimerization reaction at any desired degree of trimerization.

The invention also relates to the polyisocyanates containing isocyanurate groups obtained by this process and to their use, optionally in excess starting polyisocyanates and optionally blocked with blocking agents for isocyanate groups, as an isocyanate component for preparing polyisocyanate addition products.

DETAILED DESCRIPTION OF THE INVENTION

In the process according to the invention, diisocyanates corresponding to formula (1), which are present as a mixture of homologs and isomers, are used as starting component a). These diisocyanates are prepared by the hydrogenation of diamines corresponding to formula (2) to provide diamines corresponding to formula (3),

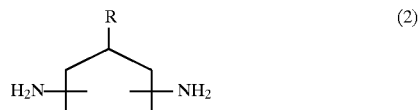

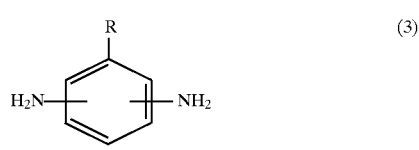

and subsequently by phosgenating the amino groups to obtain the diisocyanate of formula (1). The aromatic diamines corresponding to formula (2) can be obtained in accordance with EP 0 058 335.

Component a), which is essential to the invention, is either used as the only starting component or is used together with up to 95 NCO equivalent-%, based on the all of the isocyanate groups in the starting polyisocyanates, of other polyisocyanates b).

Optionally polyisocyanates b) include b1) aliphatic or cycloaliphatic polyisocyanates having a molecular weight of more than 139, preferably 140 to 250, such as tetramethylene diisocyanate, hexamethylene diisocyanate, dodecamethylene diisocyanate, cyclobutane-1,3 diisocyanate, cyclohexane-1,3 and/or -1,4 diisocyanate, 1-isocyanato-3,3,5-trimethyl-5-isocyanatomethyl-cyclohexane (IPDI), perhydro-2,4- and/or -2,6-diisocyanatotoluene, perhydro-2,4'- and/or -4,4'-diisocyanatodiphenylmethane and 1-isocyanato-1-methyl-4(3)-isocyanatomethylcyclohexane (IMCI);

b2) aromatic polyisocyanates having a molecular weight of more than 173, preferably 174 to 250, such as 2,4- or 2,6-toluylene diisocyanate, 2,4'-diphenylmethane diisocyanate, 4,4'-diphenylmethane diisocyanate, naphthylene-1,5 diisocyanate, 4,4',4"-triisocyantotriphenylmethane, 2,4,6-triisocyanatotoluene and polyphenyl-polymethylene polyisocyanates prepared by aniline/formaldehyde condensation and subsequent phosgenation ("crude MDI"); and b3) NCO-prepolymers having an NCO content of about 1 to 11 wt. %, which are based on the reaction product of (i) diisocyanates a) and/or polyisocyanates b1) and b2) with (ii) the known polyhydroxy compounds from polyurethane chemistry, in particular those used in two-component polyurethane coating compositions, having molecular weights of 62 to 5,000, preferably 200 to 2,000, such as those disclosed in U.S. Pat. No. 4,289,813 (herein incorporated by reference), at column 3, line 47 to column 4, line 12.

Mixtures of polyisocyanates b1) to b3) may also be used as component b) in the process according to the invention. Aliphatic and cycloaliphatic diisocyanates b1) are preferably used.

Suitable trimerization catalysts are known and include those disclosed in U.S. Pat. No. 4,289,813, herein incorporated by reference. Preferred trimerization catalysts are the Mannich bases described, for example, in DE-OS 2,551,634 (U.S. Pat. No. 4,115,373, herein incorporated by reference). The quaternary ammonium hydroxides and ammonium fluorides described in EP 330,966 and EP 355,479 (U.S. Pat. No. 4,992,548, herein incorporated by reference) are particularly preferred.

Termination of the trimerization reaction according to the invention takes place either thermally, when using thermally labile trimerization catalysts, or preferably by the addition of catalyst poisons such as those disclosed in the preceding publications. In the case of ammonium fluoride trimerization catalysts, the silylated acids disclosed in EP 508,216 (U.S. Pat. No. 5,260,481, herein incorporated by reference) may be added as catalyst poisons.

The process according to the invention may be carried out either solvent-free or in the presence of inert solvents and diluents. Inert solvents include non-polar diluents such as toluene, xylene, higher aromatic compounds, light gasoline, white spirit and $C_{12}-C_{20}$ alkylsulphonates; inert polar solvents such as esters and ketones or mixtures; and mixtures of these solvents. Mixtures of aromatic hydrocarbons and esters, e.g., a mixture of butyl acetate and xylene, are preferably used.

The trimerization reaction according to the invention is generally performed at a temperature of 10° to 200° C., preferably 20° to 80° C. The optimum reaction temperature is governed by the type of starting polyisocyanate used and the type of trimerization catalyst used, and may be determined in a simple preliminary experiment.

The trimerization reaction is generally terminated on achieving a degree of trimerization (degree of trimerization= percentage of trimerized isocyanate groups, based on the total number of isocyanate groups present in the starting polyisocyanate) of 10 to 70%. The course of the reaction can be followed, for example, by continuous determination of the refractive index.

When performing the process according to the invention in the absence of a solvent, optionally with subsequent removal of excess starting isocyanate, for example, in a thin layer evaporator, the degree of trimerization is preferably 10 to 50%. When performing the process according to the invention in the presence of a solvent, without subsequent removal of unreacted starting isocyanate, the degree of trimerization is preferably 50 to 70%.

It is a particular advantage of the process according to the invention that with a degree of trimerization of about 50 to 70% the concentration of monomeric isocyanates is surprisingly very low and subsequent removal of monomeric isocyanates by extraction or distillation is not required.

When optional starting component b) is present, previously prepared mixtures of components a) and b) are preferably used in the process according to the invention. In accordance with another embodiment of the process according to the invention it is also possible to first trimerize a portion, i.e., a maximum of 5%, of the isocyanate groups of component a) or component b) in a first reaction step, and then add the non-trimerized component a) or b) to the reaction mixture and continue the trimerization reaction to its termination point.

However, in this case (if component a) or b) are subjected to trimerization first, before adding non-trimerized component a) or b)) care must be taken that the trimerization reaction is terminated at the earliest when a further 5%, preferably a further 10%, of all the original isocyanate groups present in the starting polyisocyanates have been trimerized after completing addition of the non-trimerized starting component. Thus, for example, it is possible to trimerize a maximum of 30 NCO equivalents from 100 NCO equivalents in component a) or b), then to incorporate 100 NCO equivalents of component b) or a), to continue the trimerization reaction and, in the case of trimerizing 30 NCO equivalents from the first starting component, to terminate the reaction at the earliest after the trimerization of a total of 25 NCO equivalents.

Excess, unreacted starting isocyanates may be removed from the resulting products, in particular when the process is performed in the absence of a solvent, in known manner, for example, by thin layer distillation or extraction. After removal the polyisocyanates containing isocyanurate groups have a concentration of monomeric starting isocyanate b) of less than 3 wt. %, preferably less than 0.7 wt. %, based on resin solids. Lowering the residual monomer content of starting component a) is not necessary due to their low vapor pressure, so that concentrations of more than 3 wt. % are also acceptable.

Removal of excess starting isocyanates is preferably performed when the products are intended to be used for polyurethane coating compositions. Before their use as the isocyanate component in two-component polyurethane coating compositions, the products according to the invention may also be modified, for example by introducing urethane, urea, biuret or allophanate groups.

The products according to the invention may be used without removing excess starting isocyanates, for example, for preparing sizes.

The products according to the invention may be blocked in known manner with suitable blocking agents for isocyanate groups such as phenol, ∈-caprolactam, diethyl maleate or ethyl acetoacetate.

The products according to the invention and their blocked derivatives are valuable starting materials for preparing polyisocyanate addition products, preferably polyurethanes, by the isocyanate polyaddition process. They are particularly suited for use as the isocyanate component in two-component coating compositions, preferably polyurethane coating compositions, in combination with compounds containing two or more isocyanate-reactive groups, preferably polyols, such as those disclosed as suitable for preparing NCO prepolymers b3).

In the following examples all parts and percentage data are by weight, unless otherwise specified. All "NCO equivalent-%" are based on the total equivalents of starting isocyanates used in the examples.

EXAMPLES

Preparing a diisocyanate corresponding to formula (1)

Example 1

Ring-hydrogenation to prepare the amine of the formula (3).

In this example an aromatic diamine (2) present as a mixture of homologs and isomers in accordance with EP 0 058 335, whose alkyl chains have a length of 10 to 13 carbon atoms and an average chain length of about 12 carbon atoms, was used.

776 g of diamine, 763 g of tert.butanol and 7.7 g of hydrated ruthenium oxide were initially introduced into a 3 liter stirred autoclave. The autoclave was flushed out three times with nitrogen. Hydrogen was then introduced at a pressure of 138 bar, the mixture was heated to 180° C. with stirring and the aromatic diamine was ring-hydrogenated at a pressure of 270 to 259 bar. After a reaction time of 5 hours, no further hydrogen was taken-up. After returning the pressure in the autoclave to atmospheric pressure and separating the catalyst, the filtrate was concentrated in a rotary evaporator and the crude amine was then distilled under reduced pressure. 739 g of diamine mixture were obtained as a fraction boiling at 130° to 152° C./0.2 mbar (yield: 95%).

Example 2

A diamine (3) prepared in example 1 was used as the diamine present as a mixture of homologs and isomers in this example, its alkyl chains having a length of 10 to 13 carbon atoms with an average chain-length of about 12 carbon atoms.

2 liters of dry chlorobenzene were initially introduced into a 4 liter, four-necked flask equipped with a stirrer, thermometer, gas inlet tube and reflux condenser. 500 g of phosgene were condensed into the flask with stirring and cooling (−10° C.), then 370 g of diamine (3) dissolved in 300 g of chlorobenzene were added at −10° to −5° C., dropwise with cooling. The mixture was slowly warmed to reflux temperature while more phosgene was introduced. When the evolution of hydrogen chloride had terminated, the excess phosgene was flushed out with nitrogen and the solution was evaporated under vacuum. 345 g of a crude isocyanate mixture which had an NCO content of 19.1% (theoretical: 25.1%) and contained a small amount of biuret, according to its IR spectrum, were obtained.

300 g of the crude product were distilled under reduced pressure. 225 g of a virtually colorless mixture of diisocyanates corresponding to formula (1)

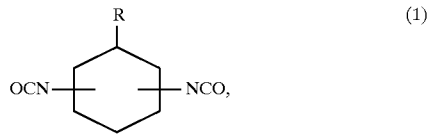

(1)

wherein

R is an alkyl chain having a length of 10 to 13 carbon atoms and an average chain length of about 12 carbon atoms, was obtained, which distilled at a temperature of 150° to 175° C. at a pressure of 0.2 mbar.

Preparing the trimerization catalysts A and B in accordance with EP 355,479 (U.S. Pat. No. 4,992, 548)

Catalyst A 32.4 g of tricaprylmethylammonium chloride (Aliquat 336 from the Fluka Co.), dissolved in 60 g of 1-butanol, were added dropwise with stirring at room temperature to 4.8 g of potassium fluoride slurried in 320 g of 1-butanol, over a period of 20 minutes. Stirring was continued for 60 minutes, insoluble constituents were filtered off and a catalyst solution was obtained which had the following property: $F^-=0.16$ mmol/g.

Catalyst B 32.4 g of tricaprylmethylammonium chloride (Aliquat 336 from the Fluka Co.), dissolved in 120 g of 1-butanol, were added dropwise, with stirring at room temperature, to 4.8 g of potassium fluoride slurried in 640 g of 1-butanol, over a period of 20 minutes. Stirring was continued for 30 minutes, insoluble constituents were filtered off and a catalyst solution was obtained which had the following property: $F^-=0.09$ mmol/g.

Trimerization examples

In trimerization examples 3 to 6, the diisocyanate mixture of example 2 was used as "diisocyanate 1."

Example 3

Partial trimerization of diisocyanate 1

322 g (0.96 mol) of diisocyanate 1 were heated to 60° C. under a nitrogen atmosphere. 1.5 g of catalyst A were then added and the progress of reaction was followed by observing the increasing refractive index. After 30 minutes at 60° to 70° C., the refractive index (25° C.) had risen from 1.4775 to 1.4879, corresponding to a decrease in NCO content from 25.0 to 19.3%. The reaction was terminated by adding 60 mg of trimethylsilyl-trifluoromethane-sulphonate (TMS triflat) dissolved in 2 g of diisocyanate 1 and the reaction mixture was stirred for a further 30 min at 80° C. A polyisocyanate mixture containing isocyanurate groups and having the following properties was obtained as a clear, colorless solution:
NCO concentration: 19.3%
Viscosity (25° C.): 327 mPa.s Example 4

Partial trimerization of diisocyanate 1

278 g (0.83 mol) of diisocyanate 1 were heated to 60° C. under a nitrogen atmosphere. 0.5 g of catalyst A were then added and the progress of the reaction was followed by observing the increasing refractive index. After 2 hours at 60° to 65° C., the refractive index (25° C.) has increased from 1.4772 to 1.4826, corresponding to a decrease in NCO content from 25.0 to 22.0%. The reaction was terminated by adding 0.3 g of a solution of 60 mg of trimethylsilyl trifluoromethane-sulphonate (TMS triflat) dissolved in 1 g of diisocyanate 1, and the reaction mixture was stirred for a further 30 min at 80° C. A polyisocyanate mixture containing isocyanurate groups and having the following properties was obtained as a clear, colorless solution:
NCO concentration: 22.0%
Viscosity (25° C.): 100 mPa.s Example 5

Co-trimerization of a mixture of diisocyanate 1 and isophorone diisocyanate (IPDI)

A mixture of 160 g (0.5 mol) of diisocyanate 1 and 444 g (2 mol) of IPDI was heated to 60° C. and then 6.1 g of catalyst A were added. The exothermic reaction which was initiated was maintained at 70° C. by cooling and was terminated after 30 min by adding 3 g of a solution of 0.7 g of trimethylsilyl trifluoromethanesulphonate (TMS triflat) dissolved in 9.3 g of IPDI. Stirring was continued at 80° C. for 30 min and a mixture containing isocyanurate groups and having an NCO content of 26.9% was obtained. After separating the unreacted diisocyanate by thin layer distillation, 240 g (yield: 40%) of a clear, pale yellow resin having an NCO content of 13.9% were obtained. According to gas chromatography of the product and the thin layer distillate obtained, the two starting diisocyanates were incorporated into the product in the same percentage by weight in which they were initially used.

Example 6

Co-trimerization of a mixture of diisocyanate 1 and hexamethylene diisocyanate (HDI)

A mixture of 165 g (0.5 mol) of diisocyanate 1 and 252 g (1.5 mol) of HDI was heated to 55° C. and then 1.2 g of catalyst B were added. The slightly exothermic reaction was maintained at 60° C. and its progress was maintained over the course of 2 hours by the further addition of 1.4 g of catalyst B. After a further hour at 60° C., the reaction was terminated by adding 0.9 g of a solution of 0.7 g of trimethylsilyl trifluoromethane-sulphonate (TMS triflat) dissolved in 9.3 g of HDI. Stirring was continued at 80° C. for 30 min and a colorless mixture containing isocyanurate groups and having an NCO content of 35.2% was obtained. After separating the unreacted diisocyanates by thin layer distillation, 86 g (yield: 21%) of a clear, almost colorless liquid having an NCO content of 18.6% and a viscosity (25° C.) of 4300 mPa.s were obtained. According to gas chromatography of the product and the thin layer distillate, about 52 g of HDI and about 34 g of diisocyanate 1 were incorporated into the trimerization product.

APPLICATION EXAMPLES

Application Example 1

Preparation of sizing liquor for internal sizing 2.5 g of a cationic starch were dissolved in 187.5 g of water at 50° C. 10 g of the trimerized isocyanate from example 4 were dissolved in this clear solution with an ULTRA-TURRAX (IKA Co.). After about 15 min, a completely homogeneous, milky dispersion was produced.

Application Example 2

Sheet making and size checking with the isocyanate dispersion from application example 1)

Paper having a weight of 80 g/m² was prepared at a pH of 7 on a paper maker of the Rapid-Köthen type of construction. The pulp consisted of 80% coniferous wood pulp and 20% hardwood pulp with a degree of beating of 35° SR. 30% precipitated $CaCO_3$ was used as filler. 0.3 or 0.5%, based on the total weight of pulp and filler, of active substance (as set forth in the following table) were added to the sizing agent. To improve retention, 0.2%, based on the total weight of pulp and filler, of a retention agent (Retaminol CO1 from Bayer AG) was also added. The paper, which was still moist, was postcondensed for 10 minutes in a drying cabinet at 90° C.

The sizing effect was tested using the Cobb test. In accordance with DIN 53 132, the absorption of water from one side of the paper over the course of 60 seconds was determined gravimetrically. The value found is a measure of the degree of sizing. The values are summarized in the following table.

| Sizing agent | Amount used (% of active substance) | Cobb value (g/m²) |
| --- | --- | --- |
| Aquapel 2B* sizing | 0.3 | 23.0 |
| agent (Comparison | 05. | 19.3 |
| Sizing liquor from | 0.3 | 16.9 |
| application example 1 | 0.5 | 17.0 |

*contains 12% active substance (product of Hercules Co.)

Application Example 3

Preparation of a water-dispersible isocyanate 74 g of the trimerized isocyanate from example 4 were reacted at 60° C. with 25 g of a polyoxyethylene polyether, which had an average molecular weight of 350 and was initiated with ethylene glycol monomethyl ether, and 1 g of dimethylethanolamine. The mixture was stirred until the isocyanate content was 10.5%. The isocyanate was readily dispersible in water in a beaker by simply stirring with a glass rod.

Application Example 4

Preparation of a water-dispersible isocyanate 74 g of the mixed trimer from example 6 were reacted with 25 g of the polyether described in application example 3 and 1 g of dimethylethanolamine. The mixture was stirred until the isocyanate content was 9.3%. The isocyanate was readily dispersible in water in a beaker by simply stirring with a glass rod.

Application Example 5

Surface sizing of paper and checking the extent of sizing

Chalk-containing paper having a weight of 80 g/m² was treated on a laboratory size-press from the Mathis Co., Switzerland, Model HF, with an aqueous dispersion of the isocyanates from examples 3 and 4. The sizing liquors also contained 5% starch (Perfektamyl from the AVEBE Co., Holland) in addition to the amounts of sizing agent set forth in the following table.

The resulting papers were dewatered by squeezing with felt and then dried at 90° C. for 10 min in a drying cabinet. The sizing effect was tested using the Cobb test, as described in application example 2.

| Sizing agent | Concentration used (% active substance) | Cobb test (g/m²) |
| --- | --- | --- |
| Aquapel 2B* sizing | 0.15 | 22.4 |
| agent (Comparison) | 0.30 | 20.4 |
|  | 0.45 | 18.7 |
| Application example 3 | 0.15 | 25.2 |
|  | 0.30 | 25.4 |
|  | 0.45 | 25.2 |
| Application example 4 | 0.15 | 24.6 |
|  | 0.30 | 32.8 |
|  | 0.45 | 23.1 |

*contains 12% active substance (product of the Hercules Co.)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a polyisocyanate containing isocyanurate groups by trimerizing a portion of the isocyanate groups of an organic polyisocyanate component comprising:

a) one or more diisocyanates corresponding to formula (1)

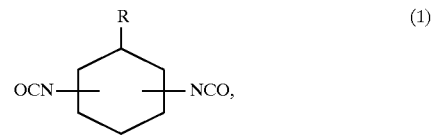

wherein:
R represents a saturated, straight-chain, aliphatic hydrocarbon group having 8 to 15 carbon atoms and
b) up to 95 NCO equivalent-%, based on the total equivalents a) and b), of one or more organic polyisocyanates other than a), in the presence of a trimerization catalyst and terminating the trimerization reaction at the desired degree of trimerization.

2. The process of claim 1, wherein polyisocyanates a) and b) are both used, which comprises:
   i) trimerizing a maximum of 30% of the isocyanate groups from one of starting polyisocyanates a) and b);
   ii) then adding the other polyisocyanate to the reaction mixture;
   iii) continuing the trimerization reaction until at least a further 5% of the isocyanate groups, based on the untrimerized isocyanate groups remaining in the starting polyisocyanates, have been trimerized; and
   iv) terminating the trimerization reaction.

3. The process of claim 1 wherein said organic polyisocyanate consists essentially of polyisocyanate a).

4. The process of claim 1 wherein polyisocyanate b) comprises hexamethylene diisocyanate or 1-isocyanato-3,3,5-trimethyl-isocyanatomethyl-cyclohexane.

5. The process of claim 2 wherein polyisocyanate b) comprises hexamethylene diisocyanate or 1-isocyanato-3,3,5-trimethyl-isocyanatomethyl-cyclohexane.

6. A polyisocyanate containing isocyanurate groups which is prepared by trimerizing a portion of the isocyanate groups of an organic polyisocyanate component comprising:
   a) one or more diisocyanates corresponding to formula (1)

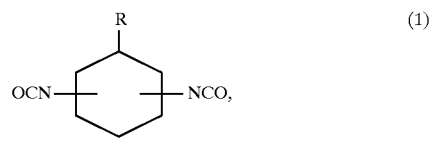

(1)

wherein:
   R represents a saturated, straight-chain, aliphatic hydrocarbon group having 8 to 15 carbon atoms and optionally
   b) up to 95 NCO equivalent-%, based on the total equivalents a) and b), of one or more organic polyisocyanates other than a), in the presence of a trimerization catalyst and terminating the trimerization reaction at the desired degree of trimerization.

7. The polyisocyanate of claim 6 wherein polyisocyanates a) and b) are both used.

8. The polyisocyanate of claim 6 wherein said organic polyisocyanate consists essentially of polyisocyanate a).

9. The polyisocyanate of claim 6 wherein polyisocyanate b) comprises hexamethylene diisocyanate or 1-isocyanato-3,3,5-trimethyl-isocyanatomethyl-cyclohexane.

10. The polyisocyanate of claim 7 wherein polyisocyanate b) comprises hexamethylene diisocyanate or 1-isocyanato-3,3,5-trimethyl-isocyanatomethyl-cyclohexane.

11. A composition containing the polyisocyanate of claim 6, wherein the isocyanate groups may optionally be blocked with a blocking agents for isocyanate groups, and a compound containing two or more isocyanate-reactive groups.

* * * * *